United States Patent
Kubota et al.

(10) Patent No.: US 8,971,151 B2
(45) Date of Patent: Mar. 3, 2015

(54) ULTRASOUND PROBE AND ULTRASOUND DIAGNOSIS APPARATUS

(71) Applicants: Kabushiki Kaisha Toshiba, Tokyo (JP); Toshiba Medical Systems Corporation, Otawara-shi (JP)

(72) Inventors: Takashi Kubota, Otawara (JO); Hiroyuki Shikata, Nasushiobara (JP); Takashi Takeuchi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 125 days.

(21) Appl. No.: 13/746,522

(22) Filed: Jan. 22, 2013

(65) Prior Publication Data
US 2013/0188446 A1   Jul. 25, 2013

(30) Foreign Application Priority Data

Jan. 24, 2012   (JP) .................................. 2012-012453

(51) Int. Cl.
*B06B 1/06* (2006.01)
*G03B 42/06* (2006.01)
*A61B 8/00* (2006.01)

(52) U.S. Cl.
CPC .............. *B06B 1/0607* (2013.01); *G03B 42/06* (2013.01); *A61B 8/00* (2013.01); *B06B 1/0622* (2013.01); *B06B 1/0637* (2013.01); *A61B 8/4483* (2013.01)
USPC ......................................................... 367/140

(58) Field of Classification Search
CPC .. B06B 1/0607; B06B 1/0637; B06B 1/0622; G03B 42/06; A61B 8/00; A61B 8/4483
USPC ......................................................... 367/7, 140
See application file for complete search history.

(56) References Cited

U.S. PATENT DOCUMENTS 3,587,561 A * 6/1971 Ziedonis ...................... 600/453
4,659,956 A * 4/1987 Trzaskos et al. .............. 310/335
(Continued)

FOREIGN PATENT DOCUMENTS

| CN | 101431941 A | 5/2009 |
| CN | 101797166 A | 8/2010 |

(Continued)

OTHER PUBLICATIONS

Combined Chinese Office Action and Search Report issued May 21, 2014 in Patent Application No. 201310027429.5 (with English translation of categories of cited documents).

*Primary Examiner* — Daniel Pihulic
(74) *Attorney, Agent, or Firm* — Oblon, McClelland, Maier & Neustadt, L.L.P.

(57) ABSTRACT

An ultrasound probe is provided that includes piezoelectric bodies, each of which is provided with electrodes on the front surface on the side from which ultrasound is emitted and a rear surface opposing the front surface. At least a part of the ultrasound probes is disposed in a curved manner. A flexible printed circuit board comprises a first part that is provided in parallel with the curved surface of the piezoelectric bodies in a circular direction on the rear surface side of the piezoelectric bodies, and a second part that extends from the first part near the end part of the arranged piezoelectric bodies and further extends to the electronic circuit, the electric circuit, or the interface. Furthermore, the flexible printed circuit board is provided with a wiring pattern that conducts between at least one electrode of the piezoelectric body and the electronic circuit, the electric circuit, or the interface.

13 Claims, 18 Drawing Sheets

(56) References Cited

U.S. PATENT DOCUMENTS

| | | | |
|---|---|---|---|
| 5,810,009 A * | 9/1998 | Mine et al. | 600/459 |
| 2011/0295124 A1 | 12/2011 | Shikata et al. | |
| 2013/0188446 A1* | 7/2013 | Kubota et al. | 367/7 |
| 2013/0303917 A1* | 11/2013 | Ona et al. | 600/459 |

FOREIGN PATENT DOCUMENTS

| | | | | |
|---|---|---|---|---|
| CN | 102218394 A | | 10/2011 | |
| JP | 05060857 A | * | 3/1993 | ............ G01S 7/52 |
| JP | 8-79895 | | 3/1996 | |
| JP | 2013150681 A | * | 8/2013 | |
| WO | WO 2013027756 A1 | * | 2/2013 | |

* cited by examiner

US 8,971,151 B2

ULTRASOUND PROBE AND ULTRASOUND DIAGNOSIS APPARATUS

CROSS-REFERENCE TO RELATED APPLICATION

This application is based upon and claims the benefit of priority from Japanese Patent Application No. 2012-012453, filed on Jan. 24, 2012; the entire contents of which are incorporated herein by reference.

FIELD

The embodiments relate to an ultrasound probe and an ultrasound diagnosis apparatus.

BACKGROUND

An ultrasound diagnosis apparatus is designed to scan subjects via an ultrasound probe to obtain organism information and image the condition inside the subjects based on the obtained organism information. More specifically, the ultrasound diagnosis apparatus transmits control signals in relation to ultrasound scanning to the ultrasound probe, transmitting ultrasound to the subject through the ultrasound probe. In addition, the ultrasound diagnosis apparatus receives reflected waves from the subject through the ultrasound probe and obtains organism information regarding the condition inside the subject. The ultrasound diagnosis apparatus produces ultrasound images based on the organism information.

The ultrasound probe is provided with an ultrasound search unit that transmits ultrasonic waves between a subject and the ultrasound probe. The ultrasound search unit has a piezoelectric body. The piezoelectric body is provided with a front electrode (for example, an earth electrode) on the front surface thereof on the side to which the ultrasonic waves are directed as well as a rear electrode (for example, a signal electrode) on the rear surface thereof. Also, the ultrasound probe is provided with a printed circuit board that is electrically connected to the piezoelectric body. The printed circuit board is provided with wiring patterns. The wiring patterns are connected to cables that transmit and receive signals to/from the ultrasound diagnosis apparatus main body through electronic circuits, electric circuits, or interfaces.

The rear electrode of the piezoelectric body of the ultrasound probe transmits and receives signals to/from the ultrasound diagnosis apparatus through the wiring pattern of the printed circuit board. For this operation, the printed circuit board is disposed on the rear surface side of the piezoelectric body, while the wiring pattern is directly or indirectly connected to the rear electrode. Also, the printed circuit board has a surface that faces the rear surface of the piezoelectric body and is extended to a cable side that is connected to the ultrasound diagnosis apparatus main body. More specifically, the printed circuit board is bent toward the cable side, the electronic circuit side such as a transmission circuit, or the electric circuit.

In addition, the ultrasound probe has an ultrasound emitting surface in the shape of a flat surface, a curved surface, or a convex surface, but the shape can be arranged in many forms depending on the ultrasound to be used. The ultrasound emitting surface of the ultrasound probe corresponds to the arrangement of the ultrasound search unit; for example, in the ultrasound emitting surface of the ultrasound probe having a convexly curved surface, the central part of the element arrangement of the ultrasound search unit is arranged so as to expand as a curved surface toward a subject. Hereinafter, the ultrasound probe may simply be referred as a "convex array probe."

DETAILED DESCRIPTION

The object of the embodiments is to provide an ultrasound probe with a printed circuit board which is easily pulled out even if an ultrasound emitting surface has a convex surface, a curved surface, or a concave surface.

The ultrasound probe according to the embodiment comprises multiple piezoelectric bodies, an electronic circuit, an electric circuit or an interface, and a flexible printed circuit board. Each piezoelectric body is provided with electrodes on the front surface of the side from which ultrasound is emitted and the rear surface opposing the front surface, with at least a part of the piezoelectric bodies disposed in a curved manner. The electronic circuit, the electric circuit, or the interface transmits and receives electric signals to/from the piezoelectric bodies. The flexible printed circuit board includes a first part that is disposed in parallel with the curved surface of the piezoelectric bodies in a circular direction on the rear surface side of the piezoelectric bodies, while a second part extending from the first part near the end part of the arranged piezoelectric bodies further extends to the electronic circuit, the electric circuit, or the interface. Furthermore, the flexible printed circuit board is provided with wiring patterns conducting between at least one electrode of the piezoelectric body and the electronic circuit, the electric circuit, or the interface.

An ultrasound search unit according to the embodiment and a manufacturing method thereof, along with an ultrasound probe will be described below with reference to FIGS. 1 to 18.

First Embodiment (Structure of an Ultrasound Probe)

Figure 1:
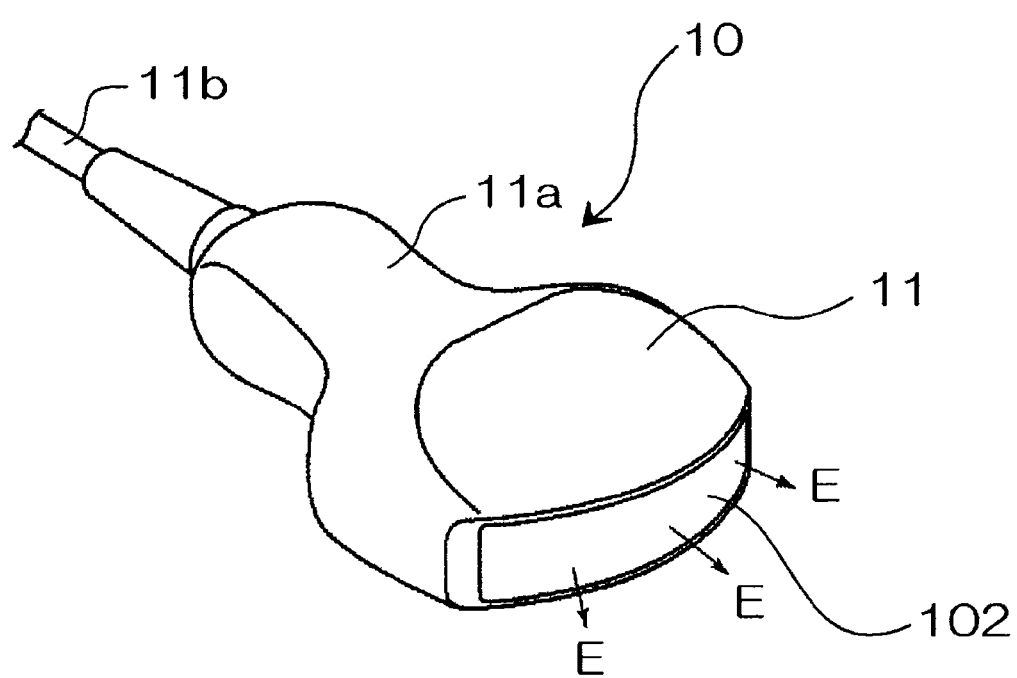
FIG. 1 is a perspective view showing an ultrasound probe according to a first embodiment.
Figure 2:
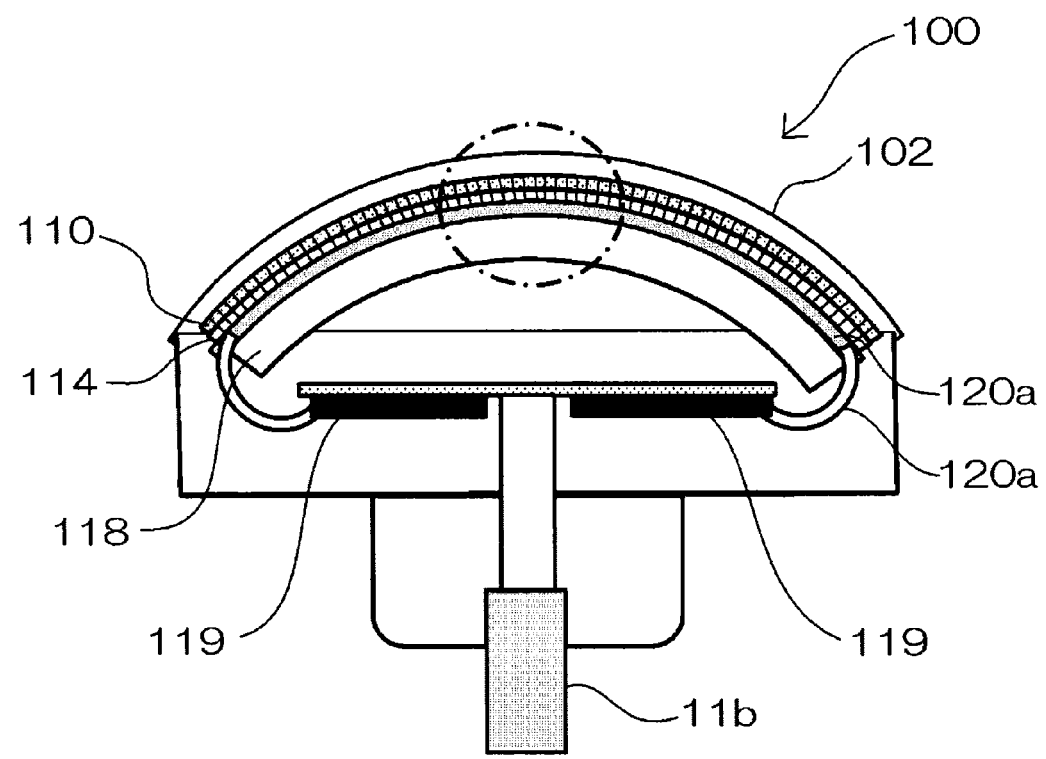
FIG. 2 is a cross-sectional view showing the internal structure of the ultrasound probe according to the first embodiment.
Figure 3:
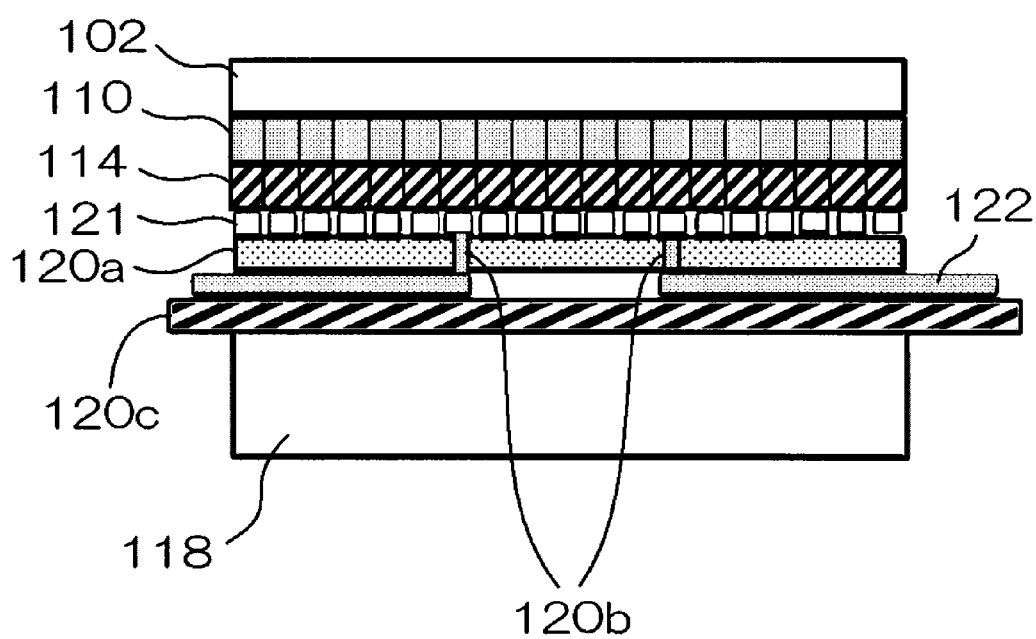
FIG. 3 is an enlarged view showing part of the structure shown in FIG. 2.

A brief overview of an ultrasound probe 10 and an ultrasound search unit 100 according to the first embodiment will be described with reference to FIGS. 1 to 13. FIG. 1 is a perspective view showing an example of the ultrasound probe 10 according to the embodiment. FIG. 2 is a cross-sectional view showing the internal structure (such as the ultrasound search unit 100, etc.) of the ultrasound probe 10 according to the first embodiment. FIG. 3 is an enlarged view of the part encircled by a dotted line in FIG. 2.

In FIG. 2, a detailed description of a first flexible printed circuit board 120a is omitted. Also, the entire form of the arranged elements of the ultrasound search unit and the arrangement, along with the number of the piezoelectric bodies shown in FIG. 2 are merely examples, and other arrangements can be employed. FIG. 3 is an enlarged view of the part encircled by a dotted line in FIG. 2, wherein the arranged elements are illustrated linearly instead of the actual curved form.

In addition, in the description below, the direction from a rear surface member 118 to an acoustic matching layer 110 as well as the direction in which the ultrasound is emitted from the ultrasound search unit 100 (the direction of "E" in FIG. 1) may be referred to as "frontward." Similarly, the direction opposing "frontward" may be referred to as "backward." The front side surface of each element of the ultrasound search unit 100 (such as the piezoelectric bodies 114, the rear surface member 118, and the first flexible printed circuit board 120a, etc.) may be referred to as the "front surface," while the rear side surface of each element may be referred to as the "rear surface."

As shown in FIG. 1, the ultrasound probe 10 has a case 11 that includes a gripping part 11a and a cable 11b. Also, the case 11 stores the ultrasound search unit 100 (see FIG. 2). As shown in FIG. 1, the part of the case 11 of the ultrasound probe 10 on the opposite side of the cable 11b has a convex curved surface. The case 11 is provided on the convex curved surface with an acoustic lens 102 that is formed to match the shape of the convex curved surface. The acoustic lens 102 serves as an ultrasound emitting surface in the ultrasound probe 10. The ultrasound probe 10 shown in FIG. 1 is merely an example, and other types of ultrasound probes can be employed. For example, an ultrasound probe having an ultrasound emitting surface shaped as a concave curved surface may be employed.

The structures of the ultrasound probe 10 and the ultrasound search unit 100 according to the first embodiment will be described below. As shown in FIG. 1, the ultrasound probe 10 is configured by comprising the case 11 for supporting the acoustic lens 102 that serves as a contacting surface with a subject, and a cable 11b that is connected to part of the case 11 on the opposite side of the acoustic lens 102. The ultrasound probe 10 is provided inside thereof with an ultrasound search unit 100 that includes piezoelectric bodies 114, etc. As shown in FIG. 2, the acoustic matching layers 110 and the piezoelectric bodies 114 of the ultrasound search unit 100 are disposed so as to expand forward from the end sides to the front side thereof. More specifically, the ultrasound search unit 100 is arranged to have a convex curved surface. In the structure shown in FIG. 2, the acoustic matching layers 110 and the piezoelectric bodies 114 are arranged in a substantially arc shape (for example, a convex array). The acoustic lens 102 is formed in a substantially arc shape to correspond to the arrangements of those elements.

In the example of the embodiment shown in FIGS. 2 and 3, the ultrasound search unit 100 comprises the acoustic matching layers 110, the piezoelectric bodies 114, the rear surface member 118, and the first flexible printed circuit board 120a, etc. In this example, the piezoelectric bodies 114 are disposed in a one-dimensional manner. As shown in FIG. 3, each piezoelectric body 114 is provided on the front surface side thereof with the acoustic matching layer 110. Also, the piezoelectric bodies 114 are provided on the rear side thereof with the rear surface member 118, and the first flexible printed circuit board 120a is provided between the rear surface member 118 and the piezoelectric bodies 114. The acoustic matching layers 110 of the ultrasound search unit 100 are provided on the front surfaces thereof with the acoustic lens 102.

In addition, the ultrasound search unit 100 is provided with a second flexible printed circuit board (not shown) that transmits electric signals from the electrode on the front side of the piezoelectric bodies 114 (hereinafter, referred to as a "front electrode") to the first flexible printed circuit board 120a. The second flexible printed circuit board may be placed, for example, in front of the acoustic matching layer 110.

[Piezoelectric Body]

Figure 4:
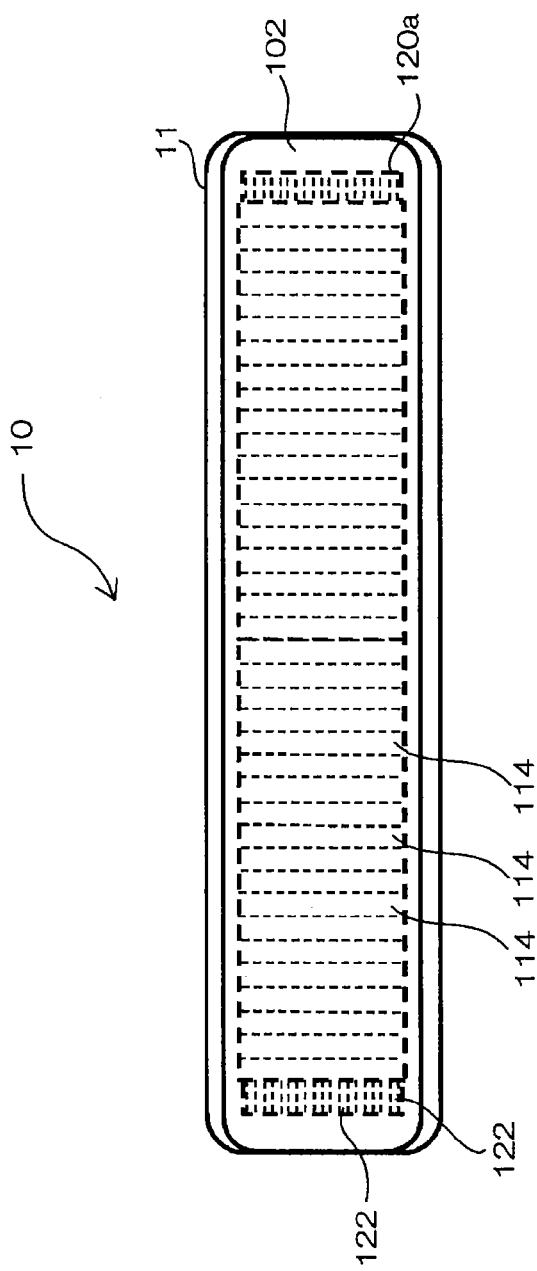
FIG. 4 shows the internal structure of the ultrasound search unit according to the first embodiment, as viewed from the ultrasound emitting surface side.

The piezoelectric body 114 acts to transform the voltage applied to the rear electrode or the front electrode into an ultrasonic pulse. Also, the ultrasonic pulse is transmitted to a subject. The piezoelectric body 114 receives reflected waves from the subject and transforms the received waves into voltage. The piezoelectric body 114 can be composed generally of PZT (lead zirconate titanate/Pb $(Zr,Ti)O_3$), barium titanate ($BaTiO_3$), PZNT ($Pb(Zn⅓Nb⅔)O3-PbTiO3$) single crystal, PMNT ($Pb(Mg⅓Nb⅔)O3-PbTiO3$) single crystal, etc. The acoustic impedance of the piezoelectric body 114 can be set, for example, to about 30Mrayl. The piezoelectric body 114 may have a thickness that is $\lambda/4$ the ultrasound wave in order to avoid influencing the rear surface side thereof. Piezoelectric bodies 114 shown in FIGS. 2 to 4 are formed in a single layer, but merely as an example, as they can also be formed in multiple layers.

[Acoustic Matching Layer]

The acoustic matching layer 110 acts to match the acoustic impedance between the piezoelectric bodies 114 and a subject. For this reason, the acoustic matching layer 110 is disposed between the piezoelectric bodies 114 and a second flexible printed circuit board (not shown) in front of the piezoelectric bodies 114 (see FIG. 3). The acoustic matching layer 110 conducts between the front surface electrodes of the piezoelectric bodies 114 and the second flexible printed circuit board, wherein said layer 110 is comprised of a conductive material or is provided with through paths. Furthermore, the acoustic matching layer may be configured from multiple layers. That is, materials with respectively different acoustic impedance are used in each layer of the acoustic matching layer. For example, a first layer of the acoustic matching layer is provided with an acoustic impedance of, for example, about 4-7Mrayl. Moreover, a second layer of the acoustic matching layer is provided with an acoustic impedance of about 9-15Mrayl. With such a configuration, it becomes possible to change the acoustic impedance between the piezoelectric bodies 114 and the acoustic lens 102 step by step, thereby accomplishing acoustic matching with respect to the subject.

An exemplary material for the first layer of the acoustic matching layer to be used for achieving acoustic matching is carbon (isotropic graphite or graphite). Also, exemplary materials for the second layer of the acoustic matching layer to be used include machinable ceramics, a mixture of epoxy and oxide metal powder, and a mixture of epoxy and metal powder. The second acoustic matching layer may have a thickness of, for example, 100 μm to 400 μm.

[Rear Surface Member]

The rear surface member 118 absorbs extra ultrasound pulses that are emitted in the direction opposite the direction in which the ultrasound pulses are primarily emitted, thereby restricting the excessive vibrations of each piezoelectric body 114. The rear surface member 118 restricts the reflection of ultrasound pulses from the rear surface of each piezoelectric body 114 during the vibration period of the piezoelectric body 114, allowing the ultrasound pulses to be transmitted without any adverse influence. Exemplary materials of the rear surface member 118 include epoxy resin containing PZT powder or tungsten, etc., rubber containing polyvinyl chloride or ferrite powder, and porous ceramics impregnating a resin such as epoxy, etc. in terms of acoustic attenuation, acoustic impedance, etc. The rear surface member 118 may have acoustic impedance in the range of about 2Mrayl to 7Mrayl.

[Rear Step Circuit]

As shown in FIG. 2, rear step circuits 119 are provided on the cable 11b side (rear side) inside the case 11 of the ultrasound probe 10. The rear step circuits 119 are connected to the electrodes of the piezoelectric bodies 114 through the first flexible printed circuit board 120a. The rear step circuits 119 are connected to a controller (not shown) of the ultrasound diagnosis apparatus main body through the cable 11b and various interfaces. With such a configuration, the rear step circuits 119 receive control signals from the controller and transmit electric signals to the piezoelectric bodies 114 based on the received control signals. The controller receives electric signals from the piezoelectric bodies 114 and transmits electric signals to the controller of the ultrasound diagnosis apparatus main body on the basis of the received electric signals. In other words, the rear step circuits 119 function as transceiver circuits that relay electric signals between the ultrasound diagnosis apparatus main body and the piezoelectric bodies 114. The rear step circuits 119 can be provided with the function of conducting the processes of phasing and adding or delaying. The rear step circuits 119 may be comprised of ASIC. The rear step circuits 119 can be comprised of electric circuits or electronic circuits.

(First Flexible Printed Circuit Board)

The first flexible printed circuit board 120a of the ultrasound search unit 100 will be described below with reference to FIGS. 1 to 7. As shown in FIG. 2, the flexible printed circuit board 120a is placed between the rear surface member 118 and the piezoelectric bodies 114, and has a length extending to the rear step circuits 119, thereby electrically connecting the piezoelectric bodies 114 and the rear step circuits 119. The electrical connection between the piezoelectric bodies 114 and the rear step circuits 119 is made by first wiring patterns 121 and second wiring patterns 122 provided on the first flexible printed circuit board 120a.

[First and Second Wiring Patterns]

As shown in FIG. 3, rear surface electrodes (not shown), which are placed behind the piezoelectric bodies 114, are connected to the first wiring patterns 121 provided on the front surface of the first flexible printed circuit board. The configuration of the first wiring patterns 121 will be described with reference to FIGS. 3 to 7. FIG. 3 is an enlarged view of the part encircled by a dashed line in FIG. 2. FIG. 4 is a schematic view showing the internal structure of the ultrasound search unit 100 according to the first embodiment, as viewed from the side from which ultrasound waves are emitted. Furthermore, FIG. 4 shows the internal structure of the ultrasound probe 10, as viewed from a point on the imaginary line extending from the acoustic lens 102 to the rear step circuits 119 (or the cable 11b), and in said figure, the piezoelectric bodies 114, the first flexible printed circuit board 120a, etc., positioned behind the acoustic lens 102 are illustrated with broken lines.

Figure 5:
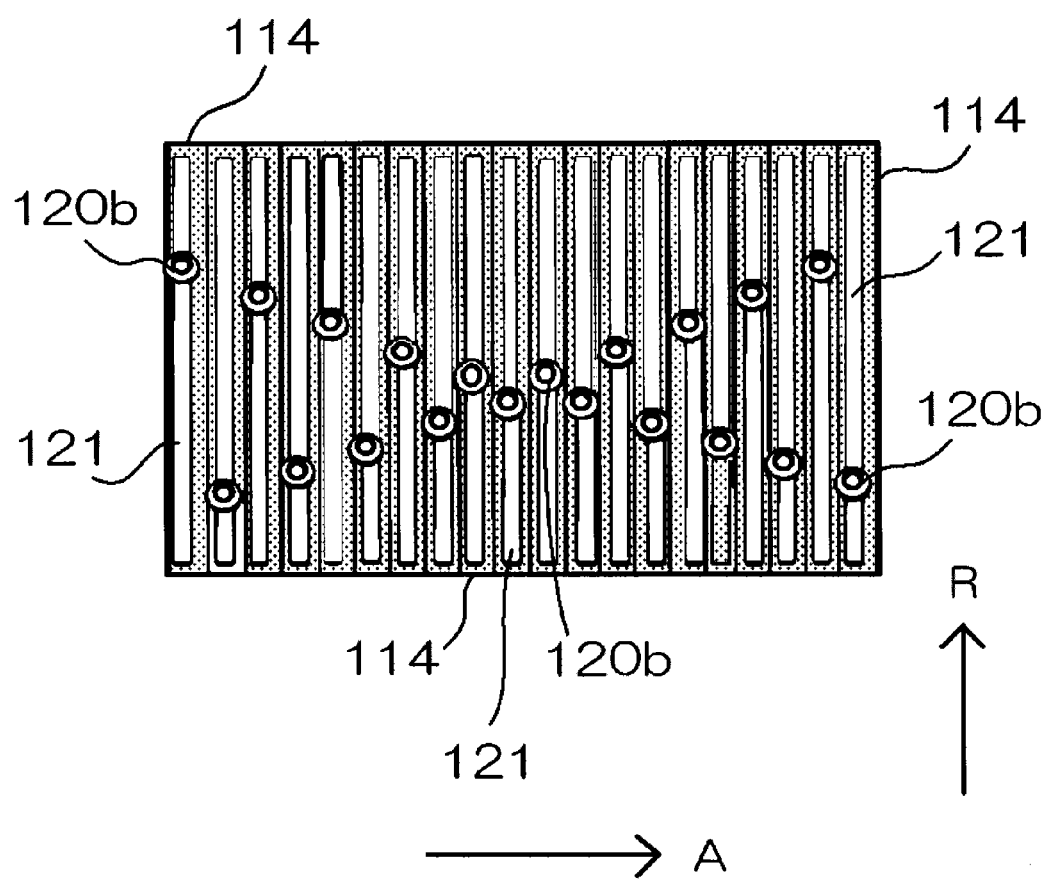
FIG. 5 shows the rear surfaces of piezoelectric bodies, first wiring patterns, and the through holes of a first flexible printed circuit board.
Figure 6:
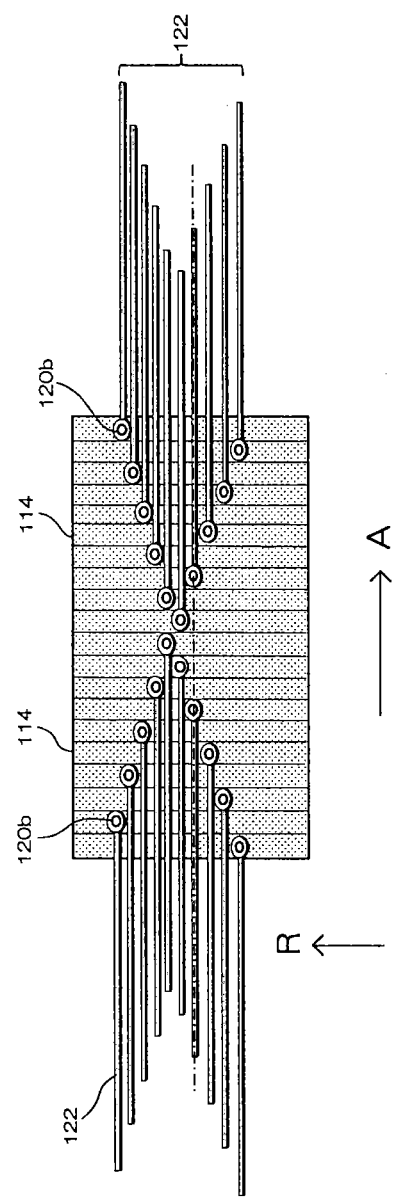
FIG. 6 shows an arrangement of the piezoelectric bodies, along with configurations of second wiring patterns and the through holes.
Figure 7:
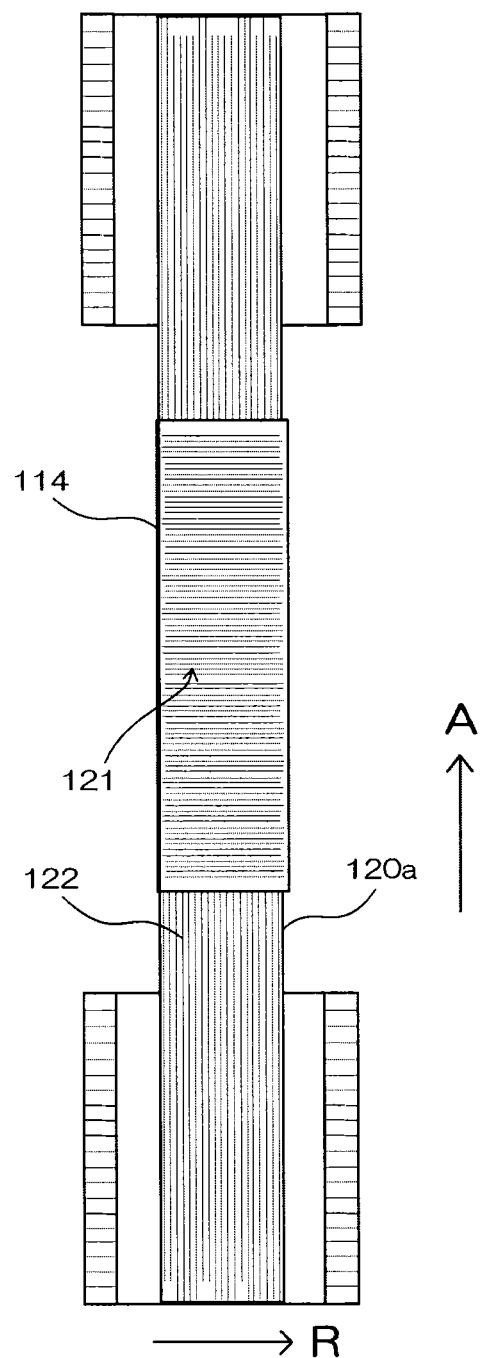
FIG. 7 briefly shows the directions in which the first wiring patterns and second wiring patterns extend.

FIG. 5 shows the rear surfaces of the piezoelectric bodies 114, the first wiring patterns 121, and the through holes 120b of the first flexible printed circuit board 120a. FIG. 6 is a schematic view showing the arrangement of the piezoelectric bodies 114, the second wiring patterns 122, and the through holes 120b. It should be noted that in FIG. 6, for clarification of the positional relationship between the direction in which the second wiring patterns 122 extend and the direction in which the piezoelectric bodies 114 extend, the first flexible printed circuit board 120a and the first wiring patterns 121 positioned between the patterns 122 and the bodies 114 are omitted. FIG. 7 is a schematic view showing the piezoelectric bodies 114, the first wiring patterns 121, and the second wiring patterns 122 of the first flexible printed circuit board 120a, as viewed from the same point that the configuration shown in FIG. 4 is viewed, schematically showing the directions in which the first wiring patterns 121 and the second wiring patterns 122 extend.

The rear surface electrode (not shown) of each piezoelectric body 114 is placed on substantially the entire area of the rear surface of the piezoelectric body 114. The first wiring patterns 121 (see FIG. 3) provided on the front surface of the first flexible printed circuit board 120a correspond to the rear surface electrodes. In the ultrasound probe 10 exemplified in FIG. 4, the pitch pattern of the first wiring patterns 121 provided on the front surface of the first flexible printed circuit board 120a corresponds to the pitch pattern of the piezoelectric bodies 114 (see FIGS. 3 and 5). In addition, as shown in FIG. 5, the first wiring patterns 121 extend on the rear surfaces of the piezoelectric bodies 114 in the longitudinal direction (in the lens direction R), and have substantially the same length as that of the longitudinal length of the rear surface electrodes.

Moreover, as shown in FIG. 3, the first flexible printed circuit board 120a has through holes 120b that pass through the printed circuit board 120 from the front surface to the rear surface thereof. FIG. 3 shows only part of the through holes 120b. As shown in FIG. 5, the front ends of the through holes 120b overlap the first wiring patterns 121, allowing the first wiring patterns 121 and the through holes to conduct with each other.

Moreover, as shown in FIG. 6, the second wiring patterns 122 are provided on the rear surface side of the first flexible printed circuit board 120a. As shown in FIG. 7, the second wiring patterns 122 extend in the direction in which the piezoelectric bodies 114 are arranged (in the array direction A), and are led outward from the arranged piezoelectric bodies 114. Also, The second wiring patterns 122 overlap the rear ends of the through holes 120b, allowing the second wiring patterns 122 and the through holes 120b to be conducted. With such a configuration, the rear surface electrodes of the piezoelectric bodies 114 are conducted to the second wiring patterns 122 via the first wiring patterns 121 and the through holes 120b of the first flexible printed circuit board 120a.

In addition, as described above, the piezoelectric bodies 114 exemplified in FIG. 2 are arranged in a curved manner, with part of the first flexible printed circuit board 120a extending along the rear surfaces of the piezoelectric bodies 114 and having a surface that is in parallel with the array direction A. As shown in FIG. 2, the rear step circuits 119 are positioned behind the center of the arranged piezoelectric bodies 114. The first flexible printed circuit board 120a is bent such that both ends thereof adjacent to the ends of the arranged piezoelectric bodies 114 extend toward the rear step circuits 119 positioned behind the piezoelectric bodies 114. Accordingly, the first flexible printed circuit board 120a extends outward from the arranged piezoelectric bodies 114 once at regions where it overlaps with the piezoelectric bodies 114, and is bent towards the center and rear side of an arrangement near the ends of the arranged piezoelectric bodies 114. The first flexible printed circuit board 120a bent towards the rear step circuits 119 side further extends to the rear step circuits 119.

The second wiring patterns 122 extend in the direction that the first flexible printed circuit board 120a extends behind the first flexible printed circuit board 120a, and are connected to the rear step circuits 119. More specifically, the second wiring patterns 122 have first parts that are in parallel with the curvedly arranged piezoelectric bodies 114 in areas in which the first flexible printed circuit board 120a overlaps the rear surfaces of the piezoelectric bodies 114. Furthermore, the second wiring patterns 122 have second parts extending from the first parts near the ends of the arranged piezoelectric bodies 114. The second parts of the second wiring patterns 122 are bent together with the first flexible printed circuit board 120a and further bent toward the center of the arranged piezoelectric bodies 114. In this manner, the ends of the second wiring patterns 122 are extended and connected to the rear step circuits 119.

[Disposition of the Through Holes]

As is clear from the above description, the first wiring patterns 121 are disposed in the lens direction R of the piezoelectric bodies 114, while the second wiring patterns 122 are disposed in the array direction A of the piezoelectric bodies 114. Accordingly, as shown in FIG. 7, the first wiring patterns 121 and the second wiring patterns 122 are adapted to cross each other orthogonally. The second wiring patterns 122 are connected to the respective rear surface electrodes, each of which is formed in an independent manner. Further, the second wiring patterns 122 are displaced with one another in the lens direction on the rear surface of the first flexible printed circuit board 120a. Accordingly, as shown in FIGS. 5 and 6, the through holes 120b are also displaced in the lens direction R on the first flexible printed circuit board 120a.

Moreover, as shown in FIG. 6, the arranged piezoelectric bodies 114 are divided in the center thereof into two groups comprising one end side (the right side from the center) and the other end side (the left side from the center) in the array direction A. More specifically, with the division of the piezoelectric bodies 114 in the center thereof, the second wiring patterns 122 are divided into two groups, wherein one group extends from the rear surfaces of the one group of piezoelectric bodies 114 while the other group extends from the rear surfaces of the other group of piezoelectric bodies 114. Also, as shown in FIG. 6, the second wiring patterns 122 connected to each rear surface electrode is extended towards one side of the arrangement. In the same manner, the second wiring pattern 122 extended from each rear surface electrode of the other group extends to the other side of the arrangement.

As an example for the configuration of the abovementioned second wiring pattern 122 and the through holes 120b, in the example of FIGS. 5 and 6, the through holes 120b are disposed as described below. That is, the through holes 120b are disposed on the diagonal lines of the arranged piezoelectric bodies 114 in the area in which the first flexible printed circuit board 120a overlaps the rear surfaces of the piezoelectric bodies 114. More specifically, the through holes 120b are displaced in the lens direction R, while the second wiring patterns 122 are divided into two groups based on the extending directions of the patterns 122, wherein the second wiring patterns 122 are disposed orthogonally in the extending direction of the first wiring patterns 121 (see FIG. 7).

[Insulation Layer]

As shown in FIG. 3, an insulation layer 120c is provided between the second wiring patterns 122 of the first flexible printed circuit board 120a and the rear surface member 118. However, it should be noted that the ultrasound search unit 100 shown in FIG. 3 is merely an example of the embodiment. In other words, possible configurations included in the embodiment may or may not include the insulation layer 120c between the second wiring patterns 122 of the first flexible printed circuit board 120a and the rear surface member 118.

(Connection Between the Ultrasound Search Unit and External Devices)

An example of the connecting configuration of the ultrasound probe 10 according to the first embodiment and the ultrasound diagnosis apparatus main body will be described below. The ultrasound probe 10 has an interface for electrically connecting with the ultrasound diagnosis apparatus main body. In the example shown in FIG. 1, the cable 1ib serves as the interface. The ultrasound probe 10 is electrically connected to the ultrasound diagnosis apparatus main body through the first and second wiring patterns 121, 122 of the first flexible printed circuit board, the second flexible printed circuit board (not shown), and the cable 11b, with ultrasound transferring signals transmitted therebetween.

The ultrasound probe may include inside thereof a connection substrate between the interface and the electronic circuit or electric circuit, in addition to the rear step circuits 119 that serve as transceiver circuits. In such a configuration, signals are transmitted and received between the electrodes of the piezoelectric bodies 114 and the controller of the ultrasound diagnosis apparatus main body, through the cable 11b that connects the ultrasound probe and the main body, the wiring patterns on the connection substrate, as well as the wiring patterns of the rear step circuits 119 and on the first flexible printed circuit board 120a.

For example, the ultrasound diagnosis apparatus main body transmits electric signals from the controller thereof through the cable 11b to drive and control the ultrasound probe 10. The electric signals are transmitted through the connection substrate to the rear step circuits 119. The rear step circuits 119 apply voltage to the piezoelectric bodies 114 through the first flexible printed circuit board 120a based on the signals transmitted from the controller of the ultrasound diagnosis apparatus. With such a system, ultrasound pulses are transmitted to a subject.

In addition, after receiving reflected waves from the subject, the ultrasound probe 10 transmits electrical signals converted by the piezoelectric bodies 114 to the rear step circuits 119 through the first flexible printed circuit board 120a. For example, the rear step circuits 119 provide predetermined processing (such as delay and addition) to the electric signals, and transmit the processed electric signals to the controller of the ultrasound diagnosis apparatus main body through the connection substrate and the cable 11b. The ultrasound diagnosis apparatus produces ultrasound images based on the electric signals.

(Operation and Advantageous Effect)

The operations and advantageous effects of the ultrasound probe 10 according to the first embodiment will be described below.

In the ultrasound probe 10 according to the first embodiment, the second wiring patterns 122 are placed in parallel with the array direction A of the piezoelectric bodies 114 behind the first flexible printed circuit board 120a. Also, The first flexible printed circuit board 120a has a bent form wherein both ends thereof facing the ends of the piezoelectric bodies 114 bend towards the rear step circuits 119. The second wiring patterns 122 are placed in the direction along which the first flexible printed circuit board 120a is placed and is connected to the rear step circuits 119.

With such a configuration, it is not necessary to bend the first flexible printed circuit board 120a either in the array direction A or the lens direction R, even if the ultrasound emitting surface has a convex surface, a curved surface, or a concave surface. Accordingly, it is easy to connect the wiring patterns to the rear step circuits 119.

First Modified Example

Figure 8:
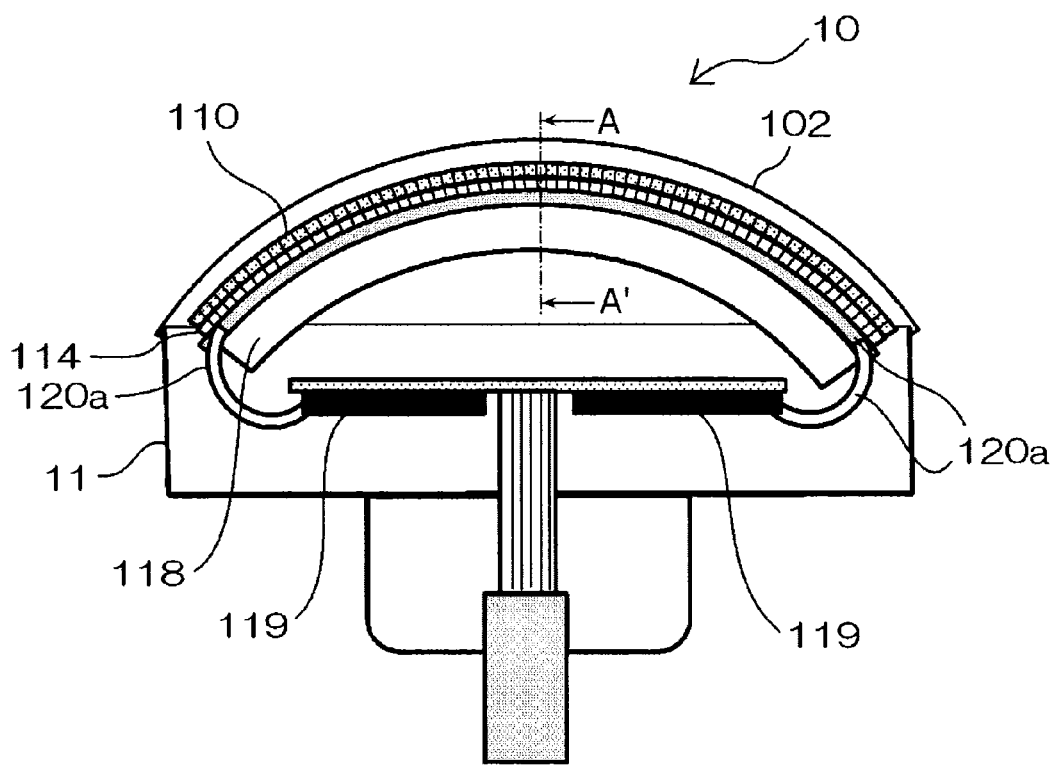
FIG. 8 is a cross-sectional view showing a first modified example of the ultrasound search unit according to the first embodiment.
Figure 9:
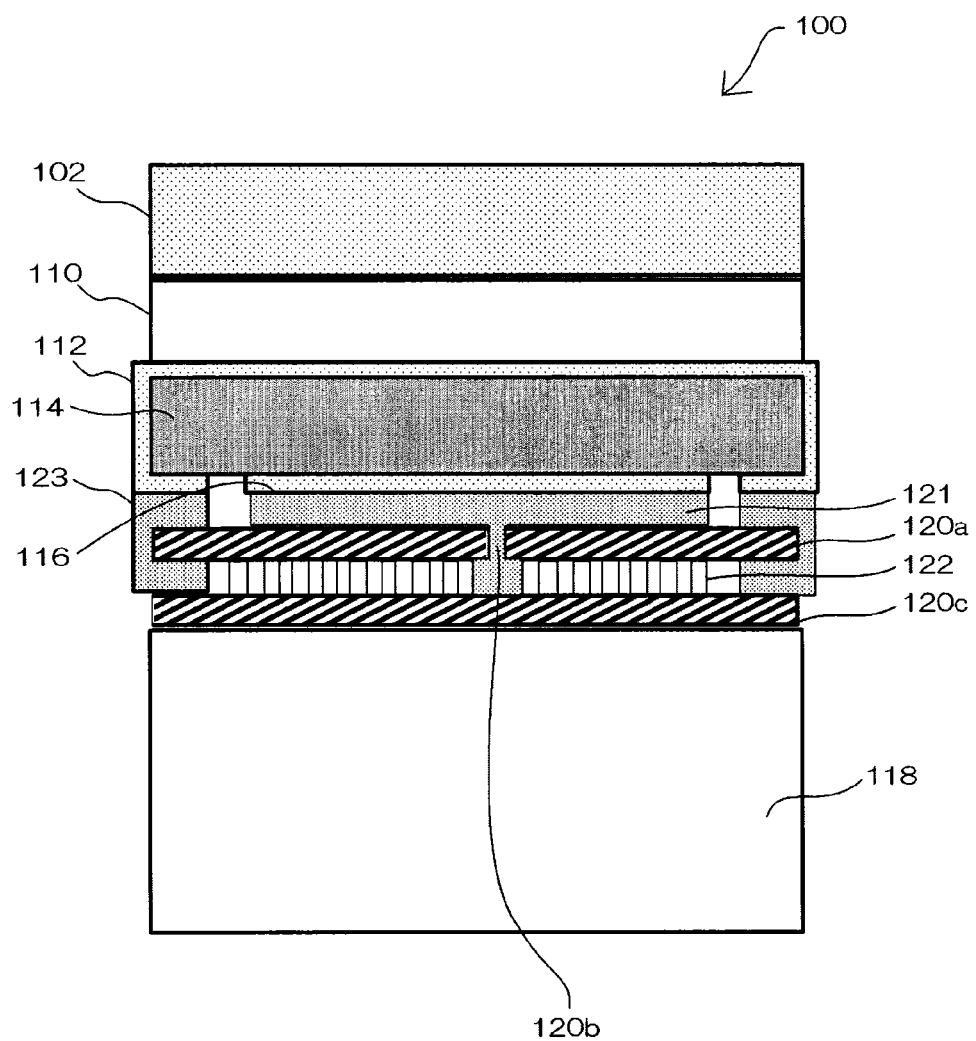
FIG. 9 is a cross-sectional view along line A-A' in FIG. 8.
Figure 10:
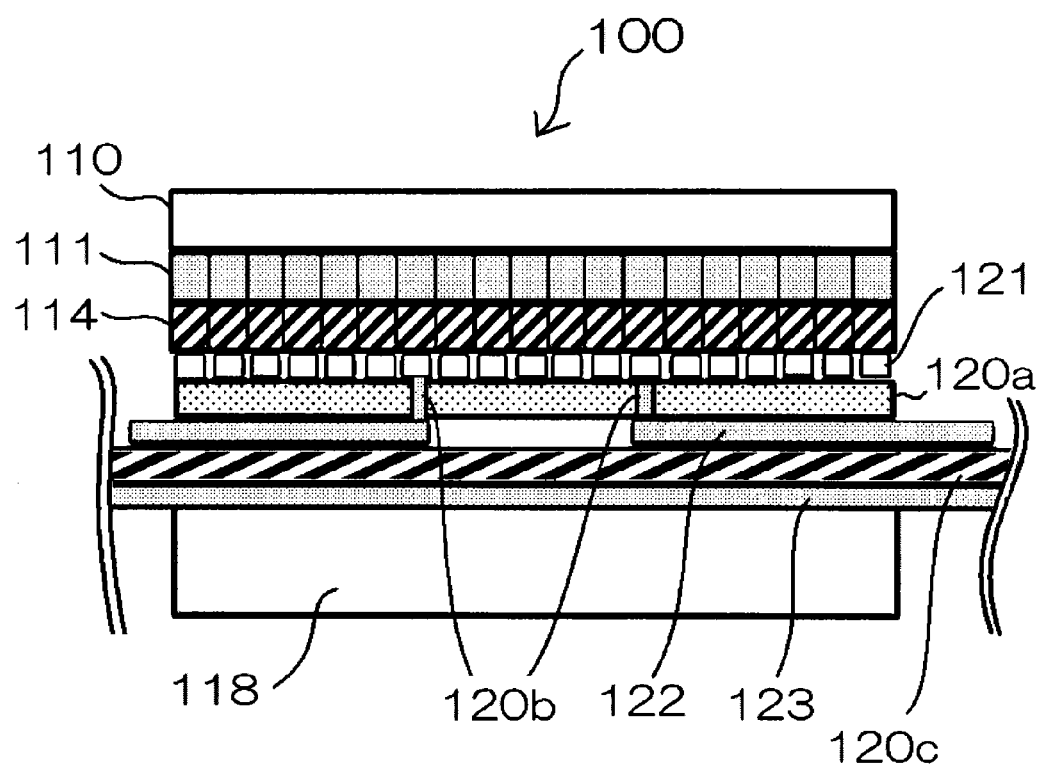
FIG. 10 is an enlarged view of a part of the configuration shown in FIG. 8.

A first modified example of the first embodiment will be described below with reference to FIGS. 8 to 11. FIG. 8 is a cross-sectional view showing the first modified example of the ultrasound search unit 100 according to the first embodiment. Also, FIG. 9 is a cross-sectional view along line A-A' in FIG. 8. FIG. 10 is a partially enlarged view of FIG. 8. Furthermore, FIG. 8 shows the first modified example corresponding to FIG. 3.

Figure 11:
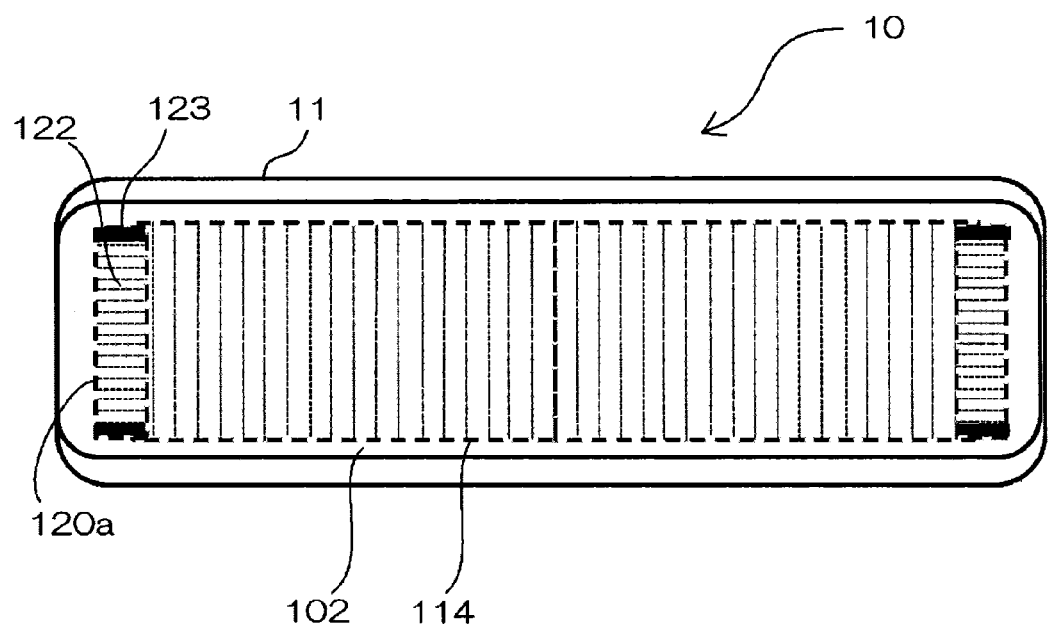
FIG. 11 shows the internal structure of the ultrasound search unit according to the first modified example, as viewed from the ultrasound emitting surface side.

FIG. 11 is a schematic view showing the internal structure of the first modified example of the ultrasound search unit 100, as viewed in the direction from the acoustic lens 102 to the rear step circuits 119 (cable 11b). In FIG. 11, the piezoelectric bodies 114 placed behind the acoustic lens 102, the first flexible printed circuit board 120a, and the second wiring pattern 112 are illustrated by dotted lines. Third wiring patterns 123 behind the first flexible printed circuit board 120a are also illustrated in FIG. 11.

In the first modified example shown in FIG. 9, a front surface electrode 112 of the piezoelectric body 114 is placed on the front surface of the piezoelectric body 114, extending to the end of the piezoelectric body 114 in the lens direction through the side surface of the piezoelectric body 114. Also, a rear surface electrode 116 is spaced from the front surface electrode 112 behind the piezoelectric body 114.

In addition, as shown in FIG. 9, the third wiring pattern 123 is placed on the end of the front surface of the first flexible printed circuit board 120a in the lens direction, facing the front surface electrode 112 behind the piezoelectric body 114. The front surface electrode 112 and the third wiring pattern 123 of the piezoelectric body 114 are connected together at the rear surface and the end of the piezoelectric body 114.

In addition, as shown in FIGS. 9 and 10, in the first modified example, the first wiring patterns 121 are also placed on the front surface of the first flexible printed circuit board 120a in the lens direction of the piezoelectric bodies 114. In the first modified example, the third wiring patterns 123 are spaced from the first wiring patterns 121. Specifically, in the first modified example, the first wiring patterns 121 are placed on the front surface of the first flexible printed circuit board 120a in the lens direction, similar to the first embodiment; however, it differs in the respect that the ends of the first wiring patterns 121 are spaced from the third wiring patterns 123.

In addition, as shown in FIG. 9, the third wiring pattern 123 is placed so as to extend around the front-end surface of the first flexible printed circuit board 120a in the lens direction to the rear surface thereof. Also, the third wiring pattern 123 is spaced from the second wiring pattern 122 in the array direction, similar to the front surface of the first flexible printed circuit board 120a.

In addition, as shown in FIG. 9, the third wiring pattern 123 can be extended around the rear surface of the insulation layer 120c through the end of the first flexible printed circuit board 120a in the lens direction. Also, as shown in FIGS. 10 and 11, the third wiring pattern 123 can be placed between the rear surface member 118 and the insulation layer 120c, and extended rearward for the ground connection, similar to the second wiring pattern 122.

In the configuration of the first modified example, it is not necessary to bend the first flexible printed circuit board 120a either in the array direction A or the lens direction R, even if the ultrasound emitting surface has a convex surface, a curved surface, or a concave surface. Accordingly, with such a configuration, the connections between the wiring patterns and the rear step circuits 119 and between the piezoelectric bodies 114 and the ground can be facilitated.

Second Modified Example

Figure 12:
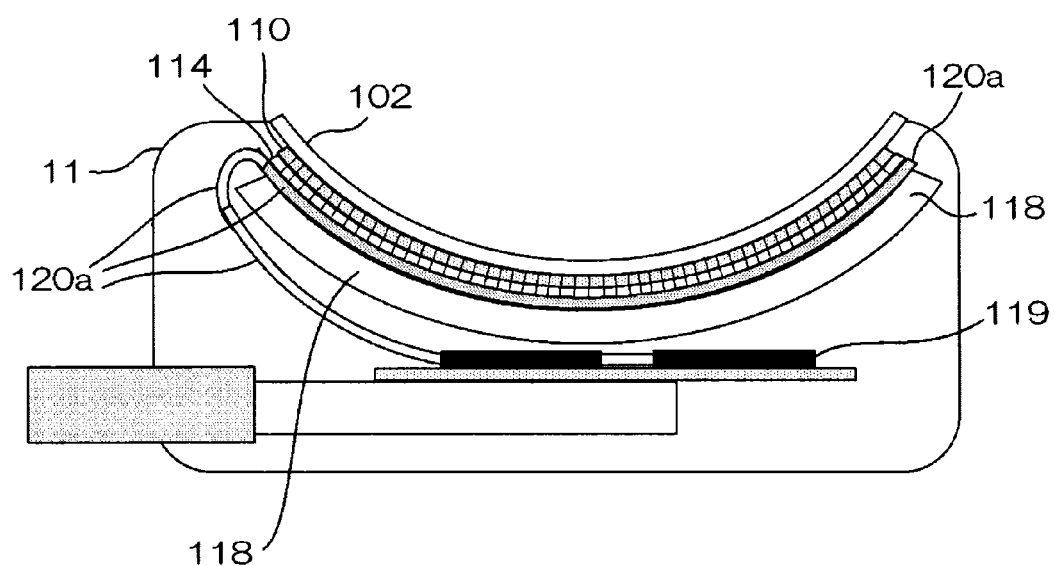
FIG. 12 is a cross-sectional view showing a second modified example of the ultrasound search unit according to the first embodiment.
Figure 13:
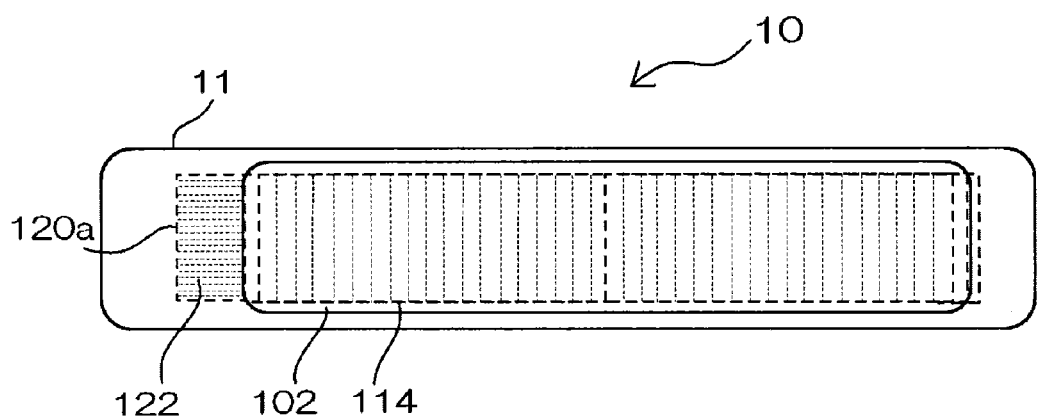
FIG. 13 shows the second modified example of the ultrasound search unit according to the first embodiment, as viewed from an acoustic lens towards the rear side thereof.

A second modified example of the first embodiment will be described below with reference to FIGS. 12 and 13. FIG. 12 is a cross-sectional view showing the ultrasound search unit 100 according to the second modified example of the first embodiment. FIG. 13 is a schematic view showing the ultrasound search unit 100 according to the second modified example, as viewed from the front side of the acoustic lens 102 to the rear side thereof. In FIG. 13, the piezoelectric bodies 114, the first flexible printed circuit board 120a, and the second wiring patterns 122 placed behind the acoustic lens 102 are illustrated by the dotted lines.

In the second modified example, the ultrasound probe 10 includes the gripping part 11a and the case 11 having a cable 11b. As shown in FIG. 12, the case 11 stores the ultrasound search unit 100. In the first embodiment described hereinbefore, the cable 11b is connected on the rear side of the acoustic lens 102 interposing the ultrasound search unit 100 therebetween. In the second modified example, the cable 11b is connected to the side surface of the case 11, as shown in FIG. 12.

In addition, as shown in FIG. 12, the case 11 of the ultrasound probe 10 has a front side forming a concave surface. The case 11 is provided on its front side with the acoustic lens 102. Moreover, the ultrasound search unit 100 comprising the piezoelectric bodies 114, etc. is provided inside the ultrasonic probe 10. Furthermore, as shown in FIG. 12, the acoustic matching layer and the piezoelectric bodies 114 in the ultrasound search unit 100 is arranged towards the center from the end of the arrangement, so as to subside towards the rear side. Specifically, the ultrasound search unit 100 is formed so as to have a concave curved surface.

The second modified example can be employed with the first modified example. Namely, in the ultrasound probe 10 of the second modified example, the front surface electrode can be provided so as to extend from the front surface of the piezoelectric body 114 to the end thereof through the side surface of the piezoelectric body 114. Also, the front surface electrode is connected to third wiring patterns 123 that are placed on the end of the front surface of the first flexible printed circuit board 120a in the lens direction. The third wiring patterns 123 are spaced from the first wiring patterns 121 on the first flexible printed circuit board 120a. Also, the third wiring patterns 123 extend from the end of the front surface of the first flexible printed circuit board 120a in the lens direction to the rear surface thereof. Also, the third wiring patterns 123 are spaced from the second wiring patterns 122 disposed in the array direction, similar to the front surface of the first flexible printed circuit board 120a. Also, the third wiring patterns 123 are placed between the rear surface member 118 and the insulation layer 120c, and extend rearward for the ground connection, similar to the second wiring patterns 122.

In the configuration of the second modified example, it is not necessary to bend the first flexible printed circuit board 120a either in the array direction A or the lens direction R, when the ultrasound emitting surface has a convex surface, a curved surface, or a concave surface. Accordingly, it is easy to connect the wiring patterns to the rear step circuits 119, and the electrodes of the piezoelectric bodies 114 to the ground.

Third Modified Example

A third modified example of the first embodiment will be described below. In the ultrasound probe 10 according to the abovementioned embodiment, the first flexible printed circuit board 120a, the insulation layer 120c, and the wiring patterns, etc. are disposed between the rear surface member 118 and the piezoelectric bodies 114. In contrast, in the third modified example, an intermediate layer is placed between the piezoelectric bodies 114 and the rear surface member 118 in addition to the first flexible printed circuit board 120a, the insulation layer 120c, the wiring patterns, etc. Furthermore, the intermediate layer is not illustrated.

The intermediate layer is placed, for example, near the rear surfaces of the piezoelectric bodies 114 and makes contact with the rear surface electrodes of the piezoelectric bodies 114. The intermediate layer can have higher acoustic impedance than the piezoelectric bodies 114 and the rear surface member 118, and have a thickness (the length in the direction from which ultrasound waves are emitted) that is about one fourth the ultrasound waves emitted from the ultrasound search unit 100. Also, the intermediate layer can be comprised of a material such as gold, lead, tungsten, mercury, or sapphire. With such an intermediate layer, the ultrasound waves emitted to the rear surfaces of the piezoelectric bodies 114 are reflected to the front surfaces side thereof (the acoustic lens acoustic lens 102 side), thereby improving the acoustic characteristics.

The first wiring patterns 121 of the first flexible printed circuit board 120a are conducted to the rear surface electrodes of the piezoelectric bodies 114 via the intermediate layer. The first wiring patterns 121 are electrically connected to the rear surface electrode through pathways provided, for example, along the circumference surface of the intermediate layer or inside the intermediate layer. In addition, by means of using an intermediate layer comprising of an electric conductive material, the first wiring patterns 121 may be electrically connected to the rear surface electrodes. Also, the first wiring patterns 121 of the first flexible printed circuit board 120a are connected to the rear step circuits 119 serving as the receiver circuits, etc.

The first modified example can be employed with the third modified example. Namely, the front surface electrode of the ultrasound probe 10 in the third modified example can be extended from the front surface to the side surface of the piezoelectric body 114. The third wiring patterns 123 to be connected to the front surface electrode are provided on the end of the front surface of the first flexible printed circuit board 120a in the lens direction. The third wiring patterns 123 can be placed so as to extend from the end of the front surface of the first flexible printed circuit board 120a in the lens direction to the rear surface thereof, be placed between the rear surface member 118 and the insulation layer 120c, and be led rearward for the ground connection, similar to the second wiring patterns 122.

The second modified example can be employed with the third modified example. Specifically, in the ultrasound probe 10 of the second modified example, the intermediate layer can be placed between the piezoelectric bodies 114 and the rear surface member 118, in addition to the first flexible printed circuit board 120a, the insulation layer 120c, and the wiring patterns.

In the second modified example, it is not necessary to bend the first flexible printed circuits 120a either in the array direction A or the lens direction R, when the ultrasound emitting surface has a convex surface, a curved surface, or a concave surface. Accordingly, this facilitates the connections between the wiring patterns and the rear step circuits 119 as well as between the electrodes of the piezoelectric bodies 114 and the ground.

Furthermore, in the first embodiment including the first, second, and third modified examples, part of the piezoelectric bodies 114, etc. can be arranged in a flat form while the rest can be arranged in a curved form. Furthermore, in the first embodiment, the curvedly arranged piezoelectric bodies 114, etc. can be placed two dimensionally in the circumference direction and in the direction perpendicular to the circumference direction.

Second Embodiment

Figure 14:
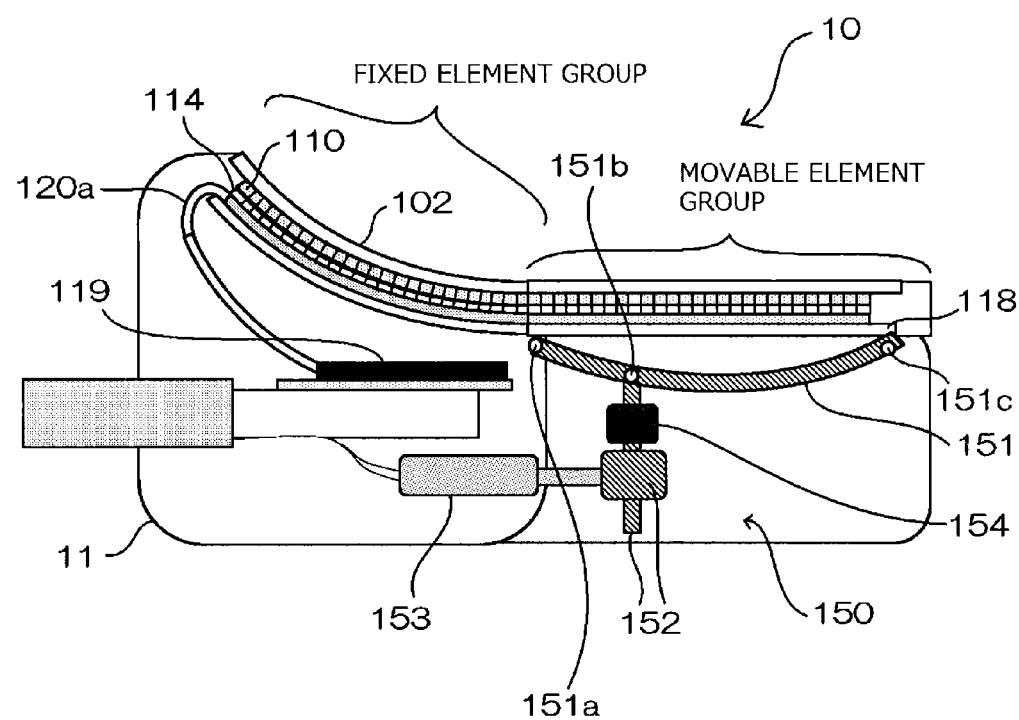
FIG. 14 is a cross-sectional view showing the internal structure (prior to operation) of the ultrasound probe according to the second embodiment.
Figure 15:
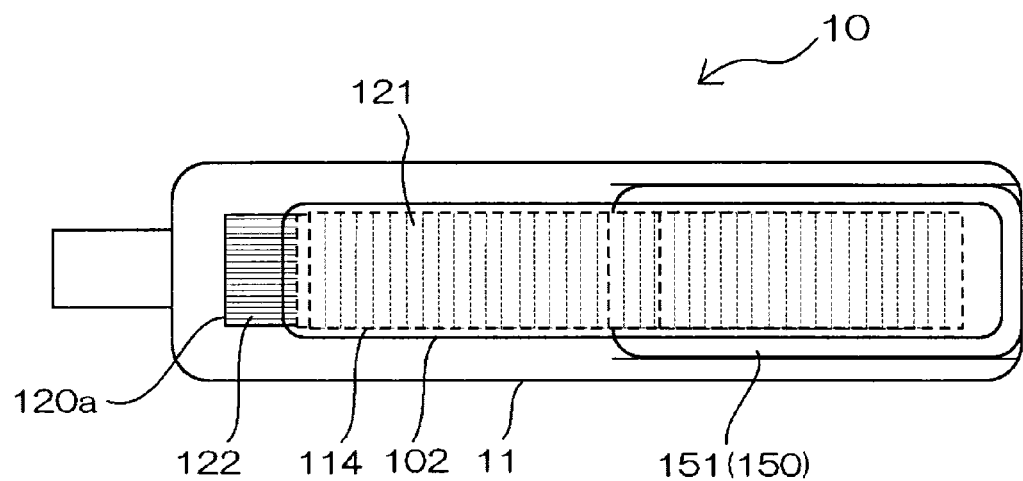
FIG. 15 shows the internal structure of the ultrasound search unit (prior to operation) according to the second embodiment, as viewed from the ultrasound emitting surface side.
Figure 16:
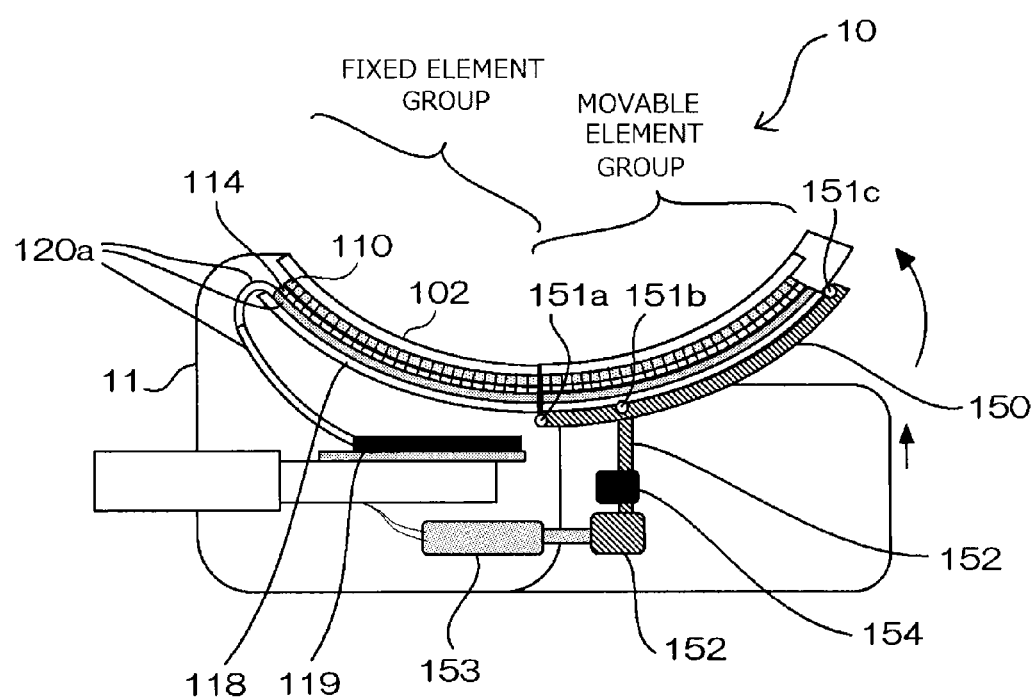
FIG. 16 is a cross-sectional view showing the internal structure (during operation) of the ultrasound probe according to the second embodiment.
Figure 17:
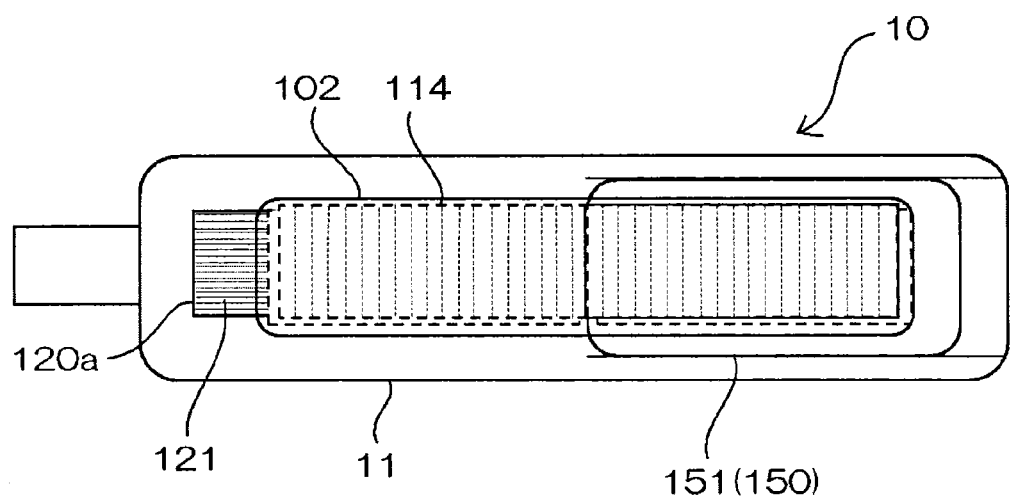
FIG. 17 shows the internal structure of the ultrasound search unit (during operation) according to the second embodiment, as viewed from the ultrasound emitting surface side.

The ultrasound probe 10 and the ultrasound search unit 100 according to a second embodiment will be described below with reference to FIGS. 14 to 17. FIG. 14 is a cross-sectional view showing the internal structure of the ultrasound probe 10 (prior to operation). FIG. 15 is a schematic view showing the internal structure of the ultrasound search unit 100, as viewed from the ultrasound-emitting surface. FIG. 16 is a cross-sectional view showing the internal structure of the ultrasound probe 10 (during operation). FIG. 17 is a schematic view showing the internal structure of the ultrasound search unit 100 (during operation) in the second embodiment, as viewed from the ultrasound-emitting surface. A description of the second embodiment will be made for elements or configurations dissimilar to the first embodiment, with similar elements or configurations omitted. In FIGS. 15 and 17, the piezoelectric bodies 114, the first flexible printed circuit board 120a, and the second wiring patterns 122 placed behind the acoustic lens 102 are illustrated by the dotted lines.

(Configuration of the Ultrasound Probe)

An example of the ultrasound probe 10 according to the second embodiment shown in FIG. 14 includes the acoustic matching layer 110, the piezoelectric bodies 114, the rear surface member 118, the first flexible printed circuit board 120a, the insulation layer 120c, and the second flexible printed circuit board (not shown). These respective elements are layered in the same order as the first embodiment.

In addition, in this second embodiment shown in FIG. 14, the piezoelectric bodies 114 are arranged one dimensionally. Part of the arranged piezoelectric bodies 114 can be re-arranged in a different form. A variable mechanism of the arranged piezoelectric bodies 114 will be described with reference to the drawings.

As shown in FIG. 14, in the ultrasound search unit 100 of the second embodiment, the elements including the acoustic lens 102, the piezoelectric bodies 114, the first flexible printed circuit board 120a, and the rear surface member 118, etc. are divided into multiple groups. The elements included in at least one of the groups can be relatively replaced in the ultrasound probe 10 by means of an element arrangement variable mechanism (see reference numeral 150 in FIG. 14 and FIG. 16). For clarity of description, the group comprising elements with positions relatively fixed in the ultrasound probe 10 may be referred to as the "fixed element group," while the group comprising elements with positions relatively moved in the ultrasound probe 10 may be referred to as the "movable element group."

The ultrasound search unit 100 according to the second embodiment is divided into the fixed element group and the movable element group. In the example shown in FIGS. 14 and 16, the fixed element group and the movable element group are divided in the center of all the arranged elements. As shown in FIG. 14, the movable element group can be arranged substantially linearly by means of the element arrangement variable mechanism in the ultrasound probe 10. As shown in FIG. 16, the movable element group can be arranged in a curved form by means of the variable mechanism in the ultrasound probe 10.

The arrangement of the fixed element group is not changed by the variable mechanism, and the relative positions of the elements thereof are fixed in the ultrasound probe 10. The fixed element group is arranged substantially symmetrical to the movable element group arranged in the curved line form. More specifically, when the movable element group is arranged in the curved line form by means of the variable mechanism 150, the ultrasound search unit 100 is formed in such a manner that the movable element group and the fixed element group are symmetrical with each other about an imaginary line extending in the center of the entire arrangement in the front-back direction.

In the example shown in FIG. 16, wherein the movable element group is arranged in a curved line form, the entire arrangement of the ultrasound search unit 100 is formed in a rearward convex shape (concave array, for example). The ultrasound probe 10 in the second embodiment may have a convex curved surface, but it is not limited to the concave curved surface.

In order to change the arrangement of the movable element group, the acoustic lens 102, the acoustic matching layer 110, the piezoelectric bodies 114, and the first flexible printed circuit board 120a, etc. may be provided with a configuration that allows them to change their positions together with the rear surface member 118 that serves as the base member. More specifically, the insulation layer 120c, the first flexible printed circuit board 120a, and the intermediate layer, etc. can be disposed on the front surface of the rear surface member 118, with the piezoelectric bodies 114, the acoustic matching layer 110, the second flexible printed circuit board (not shown), and the acoustic lens 102 disposed in front of these elements. With such a configuration, when the rear surface member 118 is bent by the variable mechanism in the form as shown in FIG. 16, the arrangement of the acoustic lens 102, the acoustic matching layer 110, the piezoelectric bodies 114, and the first flexible printed circuit board 120a, etc. is changed. The ultrasound search unit 100 including the intermediate layer operates in the same manner.

In addition, in the example shown in FIGS. 14 to 17, the first flexible printed circuit board 120a of the ultrasound search unit 100 is extended from only one end of the arrangement in the array direction, and not from both ends thereof. The first flexible printed circuit board 120a extending from said one end is bent toward the rear step circuit 119. Accordingly, the second wiring patterns 122, etc. are led to the rear step circuit 119 from the same one end. It should be noted that the ultrasound probe 10 in the second embodiment is not limited to such a configuration, and the first flexible printed circuit board 120a can be extended from both sides in the array direction and be led to the rear step circuit 119. In such a configuration, the first flexible printed circuit board 120a is provided with a length capable of coping with the movement of the movable element group.

[Brief Overview of the Element Arrangement Variable Mechanism]

The element arrangement variable mechanism 150 will be described below. As shown in FIG. 14, the variable mechanism 150 includes a holding part 151, a movable part 152, a driving part 153, and a position detector 154. The holding part 151 supports the movable element group from the rear surface side thereof. The holding part 151 is upwardly supported by the case 11 via a rotation shaft 151a. The rotation shaft 151a is positioned at the location facing the center of the arranged elements inside the case 11. The holding part 151 rotates about the rotation shaft 151a in the front-back direction of the ultrasound probe 10 on the rear side and near the center of the arranged elements.

[Holding Part of Variable Mechanism]

As shown in FIG. 16, the holding part 151 has a length extending from the rotation shaft 151a to the rear surface side end of the movable element group. The holding part 151 has a concave curved form in the direction opposite the direction from which the ultrasound waves are emitted. More specifically, as shown in FIG. 16, the holding part 151 is symmetrical to the curved line formed by the entire rear surface of the fixed element group. It should be noted that when the fixed element group has a convex curved form in the direction from which the ultrasound waves are emitted, the holding part 151 is provided with the same convex curved form.

In addition, as shown in FIGS. 14 and 16, the top end 151c of the holding part 151 on the counter side of the rotation shaft 151a is connected with the end of the arranged elements of the movable element group (such as the rear surface member 118).

[Movable Part and Driving Part of the Variable Mechanism]

As shown in FIGS. 14 and 16, the movable part 152 takes a flat plate form, a pillar form, or a shaft form, and has a connecting part 151b on one end thereof in the longitudinal direction. The holding part 151 is connected to the holding part 151 through the connecting part 151b. The movable part 152 is connected to the driving part 153. The driving part 153 has a motor, and under the operation of the driving part 153, the movable part 152 moves in the front-back direction. A system is employed by which the rotational movement of the driving part 153 can be transferred to the back-and-forth movement of the movable part 152. In such a system, when the driving part 153 is operated, components such as a shaft, etc. (not shown) rotate, and the movable part 152 connected to the driving part 153 moves frontward or rearward like a lead screw.

As shown in FIGS. 14 and 15, when the movable part 152 is in the rearward position, the movable element group is arranged linearly. When the driving part 153 is driven and the movable part 152 moves frontward in the ultrasound probe 10, the holding part 151 is pushed frontward via the connecting part 151b. The frontward movement of the holding part 151 causes the holding part 151 to rotate frontward about the rotation shaft 151a.

The frontward rotation of the holding part 151 allows the elements (such as the piezoelectric bodies 114) connected to the top end 151c of the holding part 151 to rotate together. With this movement, the front surface of the holding part 151 is gradually brought into contact with the rear surface of the movable element group. As a result, the front surface of the holding part 151 contacts the rear surface of the movable element group and pushes it frontward. Since the holding part 151 has a shape that is symmetrical with the fixed element group, the pushed movable element group changes its original arrangement to a shape that is identical to the curved shape of the front surface of the holding part 151.

[Position Detector of the Variable Mechanism]

In the example shown in FIGS. 14 and 16, the position detector 154 is disposed between the connecting part 151b of the holding part 151 and the driving part 153 inside the case 11. As shown in FIG. 14, the position detector 154 is placed in the frontward-backward movable area of the movable part 152. The position detector 154 includes a potentiometer or an encoder, whereby the displacement of the movable part 152 in the case 11 can be detected.

Detection signals of the displacement detected by the position detector 154 are transmitted to a controller (not shown). The controller receives the detection signals transmitted from the position detector 154, calculates the present positions of the movable part 152 and the holding part 151 based on the signals, and determines the arrangement of the present movable element group based on the positions of the movable part 152 and the holding part 151. The correlation between the position of the movable part 152 or the holding part 151 and the arrangement of the movable element group to be changed by the holding part 151 can be stored in advance, and the controller can determine the arrangement of the movable element group based on the stored information. The position detector 154 may be excluded if the movable element group is designed to change its arrangements in only two forms, the curved form shown in FIG. 16 and the flat form shown in FIG. 14.

In addition, the controller receives control signals from the ultrasound diagnosis apparatus main body, etc. through the cable 11b. The controller drives the driving part 153 for a predetermined magnitude based on the control signals. The controller may be designed to perform either one of the processes (the arrangement recognition or drive control). The controller may be provided in the ultrasound probe 10 or in other components (such as the ultrasound diagnosis apparatus main body). The element arrangement variable mechanism 150 is an example of a "changing unit." The "changing unit" may include the variable mechanism 150 and the controller.

(Operation)

The brief operation of changing the arrangement of the movable element group and the movement of each component of the variable mechanism 150 in the ultrasound probe 10 according to the second embodiment will be described briefly. In the description below, the operation of the variable mechanism 150 that operates to change the movable element group in the flat form shown in FIG. 14 to the curved form shown in FIG. 16 will be explained.

The controller (not shown) receives control signals from the driving part 153 in response to an operation, etc. by an operator. After the driving part 153 is driven by the control signals, the movable part 152 connected to the driving part 153 moves frontward in accordance with the movement of the driving part 153.

The movable part 152 moved frontward pushes the holding part 151 frontward via the connecting part 151b. When the holding part 151 is pushed forward, the holding part 151 is rotated forward with the rotation shaft 151a as the center. When the holding part 151 is rotated forward, the end of the array of the fixed element group, that is, the rear side of the component (the rear surface member 118) in the end of the array direction, is pushed up via the top end 151c of the holding part 151 along the rotational direction of the holding part 151.

With the holding part 151 pushed in the rotational direction, the contacting area between the front curved surface of the holding part 151 and the rear surface of the rear surface member 118, etc. of the fixed element group gradually increases. As a result, the rear surface member 118 is bent in accordance with the front surface curved line of the holding part 151 (from the stage in FIG. 14 to the stage in FIG. 16).

During the operation of the holding part 151 and the movable part 152, the position detector 154 continues to detect the movement of the movable part 152. The position detector 154 transmits detected signals of the movement to the controller (not shown). The controller controls the movement of the driving part 153 in accordance with the detected signals. The controller determines the movement of the movable part 152 for a predetermined magnitude. After determining the predetermined movement of the movable part 152, the operation of the driving part 153 is terminated.

When the controller determines that the movable part 152 has moved for the predetermined magnitude, the arrangement of the movable element group becomes symmetrical to the fixed element group about the center of the entire arrangement, as shown in FIG. 16. In this situation, the entire arrangement of the ultrasound search unit 100 has a rearward concave form.

(Operation and Advantageous Effect)

The operation and advantageous effects of the ultrasound probe 10 according to the second embodiment will be described below.

In the ultrasound probe 10 according to the second embodiment, the second wiring patterns 122 are placed in parallel with the piezoelectric bodies 114 behind the first flexible printed circuit board 120a. Also, the first flexible printed circuit board 120a is such that the portion or portions thereof at one end side or both end sides of the piezoelectric bodies 114 is/are bent toward the rear step circuit 119. The second wiring patterns 122 extend in the disposed direction of the first flexible printed circuit board 120a, and are connected to the rear step circuits 119.

With such a configuration, it is not necessary to bend the first flexible printed circuit board 120a either in the array direction A or the lens direction R, even if the ultrasound emitting surface has a convex surface, a curved surface, or a concave surface. Thus, the connection between the wiring patterns and the rear step circuits 119 can be facilitated. Furthermore, changing of the form of the arrangement can exclude the use of multiple ultrasound probes.

First Modified Example

A first modified example of the second embodiment will be described below. In the second embodiment described above, although the position detector 154 is positioned in the movable area of the movable part 152, the position detector 154 can also be provided in the driving part 153. In such a configuration, the controller detects the operation of the motor and the rotation of the shaft, etc., and determines the movement of the movable part 152 and the holding part 151 based on the detected results.

In the first modified example, it is easy to connect the wiring patterns with the rear step circuits 119, and the piezoelectric bodies 114 with the ground, similar to the second embodiment.

Second Modified Example

A second modified example of the second embodiment will be described below. In the second embodiment described above, the holding part 151 is rotated to change the arrangement of the movable element group. The second embodiment, however, is not limited to such a configuration. More specifically, it is possible to change the arrangement of the movable element group into the flat form and the curved form by rotating the end, in the array direction, of the movable element group without using the holding part 151 and the movable part 152. In one example thereof, a moving member and a guide member are provided in the case 11, wherein the moving member is connected to the end of the movable element group and rotates the end thereof, and the guide member supports the rotational movement of the moving member. The controller drives the driving part 153, moving the moving member along the guide member.

In the second modified example, the connections between the wiring patterns and the rear step circuits 119 as well as between the piezoelectric bodies 114 and the ground can be facilitated.

Third Modified Example

A third modified example of the second embodiment will be described below. In the second embodiment described above, the elements of the ultrasound search unit 100 were divided into two groups, with the arrangement of one group fixed while that of the other group can be changed. The second embodiment, however, is not limited to such a configuration. For example, the elements can be divided into three groups, wherein one of them is formed in the fixed element group while the other two are formed in the movable element groups, each of which is of an arrangement that can be adapted to move independently. In this system, variable mechanisms 150 are arranged to operate independently.

In addition, in another example, multiple groups can be formed from the movable element groups.

In the third modified example, the connections between the wiring patterns and the rear step circuits 119 as well as between the piezoelectric bodies 114 and the ground can be facilitated, similar to the second embodiment.

The first, second and third modified examples in the second embodiment can be combined with one another, and they can also be combined with the first, second, and third modified examples of the first embodiment.

Third Embodiment

An ultrasound probe 10 and an ultrasound search unit 100 according to the third embodiment will be described below with reference to FIG. 18.

Figure 18:
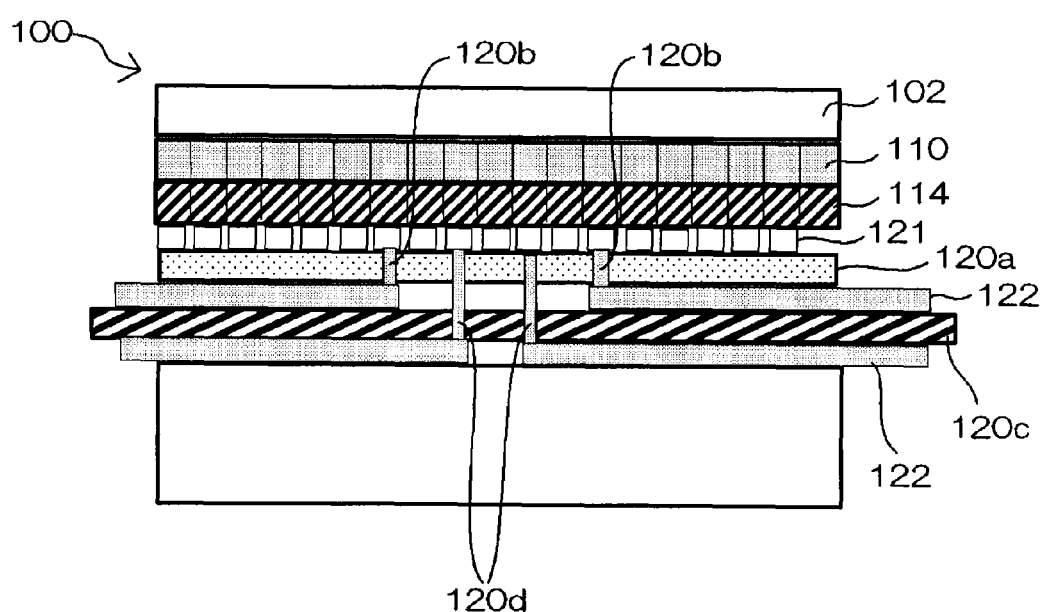
FIG. 18 is a cross-sectional view showing the internal structure of the ultrasound probe according to a third embodiment.

FIG. 18 is a cross-sectional view showing the internal structure of the ultrasound probe ultrasound probe 10. In this third embodiment, components or configurations dissimilar to the first and second embodiments will be described primarily, with descriptions of the same components or configurations omitted.

In each of the ultrasound probes 10 according to the first and second embodiments, the second wiring patterns 122 are led to the rear surface of the first flexible printed circuit board 120a, and are further led to the rear step circuits 119 through the rear surface of the first flexible printed circuit board 120a. In contrast, in the exemplified ultrasound probe 10 according to the third embodiment shown in FIG. 18, a part of the second wiring patterns 122 is led to the rear surface of the first flexible printed circuit board 120a, while the rest of the second wiring pattern 122 is led to the rear surface of the insulation layer 120c.

More specifically, as shown in FIG. 18, the second wiring patterns 122 led to the insulation layer 120c extend to the rear surface of the first flexible printed circuit board 120a through the through hole 120b on the first wiring pattern 121. A part of the second wiring patterns 122 is led to the rear surface of the insulation layer 120c behind the first flexible printed circuit board 120a. The insulation layer 120c has through holes 120d that are used to lead the second wiring patterns 122 from the front surface of the insulation layer 120c to the rear surface thereof. The led part of the second wiring patterns 122 extends in the array direction of the arranged elements in a manner similar to the second wiring patterns 122, which is led to the rear surface of the first flexible printed circuit board 120a, and is bent rearward at the end thereof in the array direction to reach the rear step circuits 119.

A third flexible printed circuit board (not shown) can be provided behind the first flexible printed circuit board 120a but not behind the insulation layer 120c, and part of the second wiring patterns 122 can be led to the rear surface thereof. In such a configuration, the insulation layer 120c can be provided behind the third flexible printed circuit board.

Furthermore, in the event that it is difficult to provide a space for the second wiring patterns 122, the second wiring patterns 122 may be formed of not only two layers but also three layers.

In the third embodiment, the connections between the wiring patterns and the rear step circuits 119 as well as between the piezoelectric bodies 114 and the ground can be facilitated, similar to the first and the second embodiments.

In addition, the surface for leading the second wiring pattern 122 (wiring for signal) expands, making it easy to lead the second wiring pattern 122.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. An ultrasound probe comprising:
   multiple piezoelectric bodies each provided with electrodes on a front surface thereof which a side of ultrasonic emission and on a rear surface opposing the front surface, with at least a part of the multiple piezoelectric bodies being disposed in a curved manner;
   an electronic circuit, an electric circuit, or an interface that transmits and receives electric signals to/from the piezoelectric bodies; and a flexible printed circuit board comprising a wiring pattern, the wiring pattern comprising:
a first part disposed substantially in parallel with the curved piezoelectric bodies in a circular direction thereof on the rear surface side of the piezoelectric bodies;
a second part extending from the first part at a location near the end part of the arranged piezoelectric bodies towards the electronic circuit, the electric circuit, or the interface; and
a wiring pattern connecting at least one of the electrodes and the electronic circuit, the electric circuit, or the interface, wherein the piezoelectric bodies are arranged in a one-dimensional manner in the circular direction of the curved surface thereof, or are disposed two-dimensionally in the circular direction of the curved surface and the direction orthogonal to the circular direction within the curved surface.

2. The ultrasound probe according to claim 1, wherein the piezoelectric bodies have a part disposed in a curved manner and a part disposed in a flat manner.

3. The ultrasound probe according to claim 1, wherein the piezoelectric bodies have a part disposed in a convex manner or a concave manner and a part disposed in a flat manner.

4. The ultrasound probe according to claim 1, wherein the piezoelectric bodies are disposed in a convex curved manner in the direction that ultrasound is emitted.

5. The ultrasound probe according to claim 1, further comprising a changing unit that changes at least a part of the arranged piezoelectric bodies into a curved shape.

6. The ultrasound probe according to claim 5, comprising a driving element that drives the changing unit.

7. The ultrasound probe according to claim 1, wherein the wiring pattern includes a first pattern group that is disposed from and parallel to the center of the arranged piezoelectric bodies to a first end side thereof, and a second pattern group that is disposed from and parallel to the center of the arranged piezoelectric bodies to a second end side thereof;
the first pattern group is conducted to each of the piezoelectric bodies that are located from the center of the arranged piezoelectric bodies to the one end side thereof; and
the second pattern group is conducted to each of the piezoelectric bodies that are located from the center of the arranged piezoelectric bodies to the second end side thereof.

8. The ultrasound probe according to claim 1, wherein the electrode disposed on the front surface of the piezoelectric body is an earth electrode, while the electrode disposed on the rear surface opposing the front surface is a signal electrode; and
the printed circuit board comprising:
a first layer provided with signal wiring that is conducted to the signal electrode;
a second layer provided with earth wiring that is conducted to the earth electrode; and
an insulation layer provided between the first layer and the second layer.

9. The ultrasound probe according to claim 1, wherein the electrode provided to the front surface of the piezoelectric body is an earth electrode, while the electrode provided to the rear surface of the piezoelectric body opposite the front surface is a signal electrode;
the printed circuit board is provided on the front surface thereof opposing the rear surface of the piezoelectric bodies with signal wiring that is conducted to the signal electrode and earth wiring that is conducted to the earth electrode; and
the signal electrode and the signal wiring are conducted while the earth electrode and the earth wiring are conducted in a region near the rear surface of the piezoelectric bodies.

10. The ultrasound probe according to claim 1, further comprising an intermediate layer between the piezoelectric bodies and the printed circuit board, said intermediate layer being conductive and having higher acoustic impedance than the piezoelectric body.

11. The ultrasound probe according to claim 1, wherein the piezoelectric bodies are arranged in the one-dimensional manner in the circular direction of the curved surface thereof.

12. The ultrasound probe according to claim 1, wherein the piezoelectric bodies are disposed two-dimensionally in the circular direction of the curved surface and the direction orthogonal to the circular direction within the curved surface.

13. An ultrasound diagnosis apparatus comprising:
the ultrasound probe according to claim 1;
an image generator configured to generate an ultrasound image based on signals received from the ultrasound probe; and
a display configured to display the ultrasound images generated in the image generator.

* * * * *